(12) United States Patent
Ennis et al.

(10) Patent No.: US 7,985,873 B2
(45) Date of Patent: Jul. 26, 2011

(54) SYNTHESIS OF PHENOLIC ESTERS OF HYDROXYMETHYL PHENOLS

(75) Inventors: Seth C. Ennis, Limerick (IE); Roland Drews, Monheim (DE); Claus Meese, Monheim (DE)

(73) Assignee: UCB Pharma GmbH, Monheim (DE)

( * ) Notice: Subject to any disclaimer, the term of this patent is extended or adjusted under 35 U.S.C. 154(b) by 401 days.

(21) Appl. No.: 12/303,829

(22) PCT Filed: Jun. 5, 2007

(86) PCT No.: PCT/EP2007/004977
§ 371 (c)(1),
(2), (4) Date: Dec. 8, 2008

(87) PCT Pub. No.: WO2007/140986
PCT Pub. Date: Dec. 13, 2007

(65) Prior Publication Data
US 2010/0168459 A1 Jul. 1, 2010

(30) Foreign Application Priority Data

Jun. 9, 2006 (EP) .................................... 06011966
Jun. 9, 2006 (IE) ................................. S2006/0433

(51) Int. Cl.
*C07C 69/035* (2006.01)
(52) U.S. Cl. ..................................................... 560/140
(58) Field of Classification Search ....................... None
See application file for complete search history.

(56) References Cited

U.S. PATENT DOCUMENTS
6,713,464 B1  3/2004  Meese et al.

FOREIGN PATENT DOCUMENTS
| WO | 94/11337 | 5/1994 |
| WO | 98/43942 | 10/1998 |
| WO | 01/35957 | 5/2001 |

*Primary Examiner* — Daniel Sullivan
*Assistant Examiner* — Yevegeny Valenrod
(74) *Attorney, Agent, or Firm* — Kenyon & Kenyon LLP

(57) ABSTRACT

The present invention provides a process for the production of a compound of formula (I) or a salt thereof, wherein R is hydrogen, a straight, branched or cyclic $C_1$-$C_6$ alkyl group or an aryl group which may optionally be substituted. This process comprises: (a) reacting a compound of formula (II), with a compound of formula (III), wherein R is as defined above and X is a leaving group, in the presence of N,N-di-isopropylethylamine.

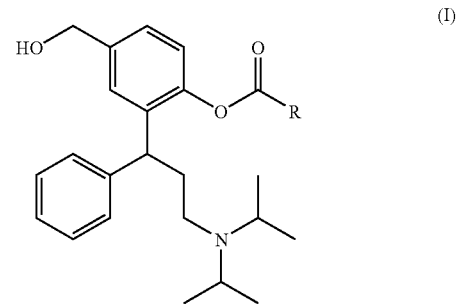

(I)

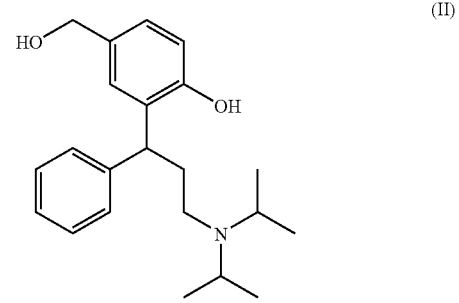

(II)

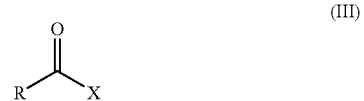

(III)

18 Claims, No Drawings

SYNTHESIS OF PHENOLIC ESTERS OF HYDROXYMETHYL PHENOLS

CROSS REFERENCE TO RELATED APPLICATION

This application is a 371 of International Patent Application No. PCT/EP2007/004977, filed Jun. 5, 2007, which claims priority to European Patent Application No. 06011966.6, filed Jun. 9, 2006, and Irish Patent Application No. S2006/0433, filed Jun. 9, 2006. The contents of these applications are hereby incorporated by reference in their entireties.

FIELD OF THE INVENTION

The present invention relates to a process for the preparation of the phenolic monoesters of 2-(3-diisopropylamino-1-phenylpropyl)-4-(hydroxymethyl)phenol which is known as the active metabolite of tolterodine (hereafter named the "active metabolite") by a synthetic route via a modified esterification procedure. The target compounds have the following formula (I):

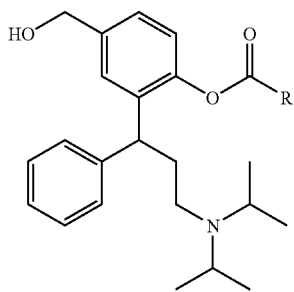

(I)

wherein R is hydrogen, a straight, branched or cyclic $C_1$-$C_6$ alkyl group or an aryl group. These groups may optionally be substituted.

A particular preferred example of the phenolic monoesters of formula (I) is fesoterodine which is chemically defined as R-(+)-isobutyric acid 2-(3-diisopropylamino-1-phenylpropyl)-4-(hydroxymethyl)phenol ester. It has the formula (Ia) depicted below.

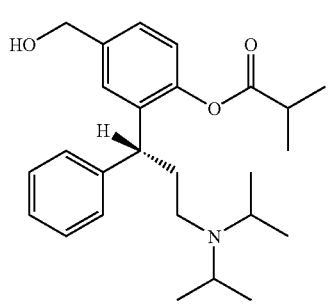

(Ia)

The active metabolite and its phenolic monoesters of formula (I) including fesoterodine are known e.g. from WO 94/11337 and U.S. Pat. No. 6,713,464, respectively.

The present invention further relates to a process for the preparation of salts and/or solvates of the compounds of formula (I), specifically including the preparation of salts of fesoterodine, and particularly the preparation of the hydrochloride or fumarate salts of fesoterodine. A particular preferred embodiment of the invention is a process for the preparation of fesoterodine hydrogen fumarate or fesoterodine hydrochloride hydrate.

BACKGROUND OF THE INVENTION

In man, normal urinary bladder contractions are mediated, (inter alia), through cholinergic muscarinic receptor stimulation. Muscarinic receptors not only mediate normal bladder contractions, but may also mediate the main part of the contractions in the overactive bladder resulting in symptoms such as urinary frequency, urgency and urge urinary incontinence.

After administration of fesoterodine and other phenolic monoesters of formula (I) to mammals, such as humans, these compounds are cleaved to form the active metabolite. The active metabolite is known to be a potent and competitive muscarinic receptor antagonist (WO 94/11337). Therefore, fesoterodine and other phenolic esters of formula (I) represent potential prodrugs for the active metabolite, and are drugs which are effective in the treatment of overactive bladder with symptoms of urge urinary incontinence, urgency, and urinary frequency, as well as detrusor hyperactivity (as described e.g. in U.S. Pat. No. 6,713,464).

A synthesis for the production of the active metabolite as well as its phenolic monoesters such as fesoterodine has previously been described, e.g. in U.S. Pat. No. 6,713,464.

According to U.S. Pat. No. 6,713,464, the phenolic monoesters of the active metabolite are prepared as follows:

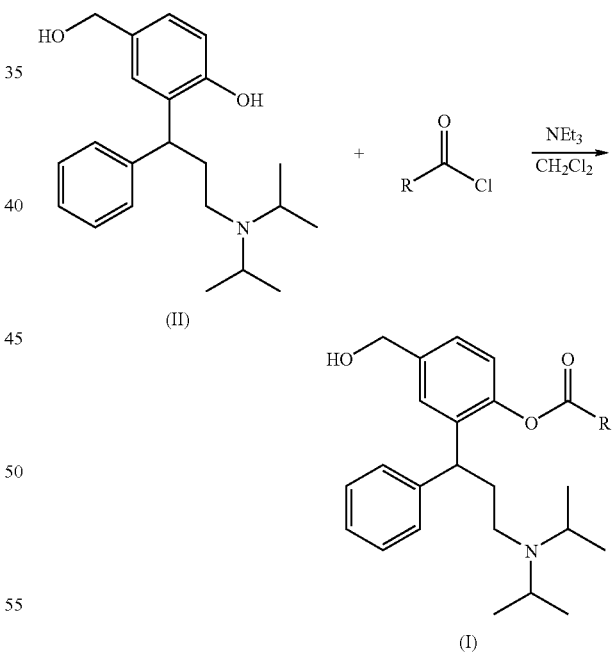

A solution of 2-(3-diisopropylamino-1-phenylpropyl)-4-hydroxymethylphenol (the active metabolite) and the corresponding acid chloride in dichloromethane is cooled to 0° C. Subsequently, a solution of triethylamine in dichloromethane is added dropwise during 5-10 minutes under stirring. Stirring is continued for 18 h at room temperature, and then the mixture is washed with water, aqueous sodium hydrogen carbonate, and water. The organic phase is dried over sodium sulphate and evaporated under reduced pressure. The oily residues obtained are finally exposed to high vacuum for 2-4 h, to remove the remaining traces of solvents.

The synthesis of the active metabolite, which is used as the starting material in the present invention, is known in the prior art. WO 94/11337 and WO 98/43942 both describe a multi-stage process to synthesize the active metabolite.

In accordance with general acylation procedures, triethylamine acts as an acid scavenger in the prior art process, thereby drawing the equilibrium of the reaction to the side of the end products, and increasing the yield of the phenolic monoester of the active metabolite. However, contrary to the skilled person's expectations, the applicant realized that the chemoselectivity of the reaction is superior when the reaction is performed in the absence of triethylamine.

As a consequence, there was a desire for a base which acts as a catalyst for the regioselective acylation and in comparison to triethylamine results in a higher yield and purity of the phenolic monoesters of formula (I).

Surprisingly, this object could be attained by performing the reaction in the presence of N,N-diisopropylethylamine (Huenig's base).

SUMMARY OF THE INVENTION

Accordingly, the present invention provides a process for the production of a compound of formula (I) or a salt thereof

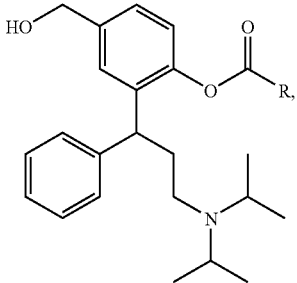

(I)

wherein R is hydrogen, a straight, branched or cyclic $C_1$-$C_6$ alkyl group or an aryl group, wherein the alkyl and aryl groups may optionally be substituted, comprising (a) reacting a compound of formula (II)

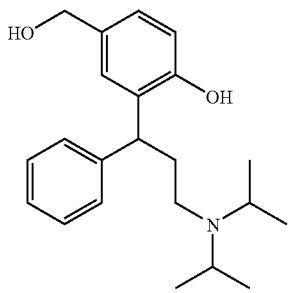

(II)

with a compound of formula (III)

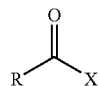

(III)

wherein R is as defined above and X is a leaving group, characterized in that the reaction is performed in the presence of N,N-diisopropylethylamine.

DETAILED DESCRIPTION OF THE INVENTION

The present invention relates to an improved process for the preparation of the phenolic monoesters of the active metabolite of formula (I):

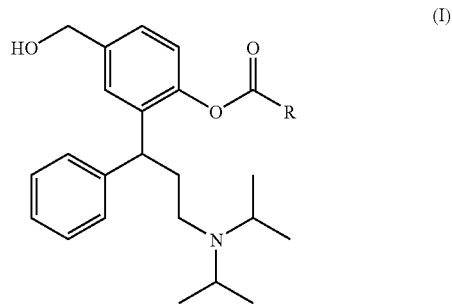

(I)

wherein R is hydrogen, a straight, branched or cyclic $C_1$-$C_6$ alkyl group or an aryl group. These alkyl or aryl groups may optionally be substituted. R is preferably hydrogen, a straight, cyclic or branched $C_1$-$C_6$ alkyl group, which is most preferably unsubstituted, or R represents a phenyl or naphthyl group, wherein the phenyl or naphthyl groups are either unsubstituted or are substituted with one or more substituents selected from halogen, $C_1$-$C_6$ alkyl group, a $C_1$-$C_6$ alkoxy group, nitro and hydroxyl. Preferred monoesters of formula (I) which may be produced using the process of the present invention are the ones disclosed in U.S. Pat. No. 6,713,464, such as:

(±)-formic acid 2-(3-diisopropylamino-1-phenylpropyl)-4-hydroxymethylphenyl ester,
(±)-acetic acid 2-(3-diisopropylamino-1-phenylpropyl)-4-hydroxymethylphenyl ester,
(±)-propionic acid 2-(3-diisopropylamino-1-phenylpropyl)-4-hydroxymethylphenyl ester,
(±)-n-butyric acid 2-(3-diisopropylamino-1-phenylpropyl)-4-hydroxymethylphenyl ester,
(±)-isobutyric acid 2-(3-diisopropylamino-1-phenylpropyl)-4-hydroxymethylphenyl ester,
R-(+)-isobutyric acid 2-(3-diisopropylamino-1-phenylpropyl)-4-hydroxymethylphenyl ester,
(±)-2,2-dimethylpropionic acid 2-(3-diisopropylamino-1-phenylpropyl)-4-hydroxymethylphenyl ester,
(±)-2-acetamidoacetic acid 2-(3-diisopropylamino-1-phenylpropyl)-4-hydroxymethylphenyl ester,
(±)-cyclopentanecarboxylic acid 2-(3-diisopropylamino-1-phenylpropyl)-4-hydroxymethylphenyl ester,
(±)-cyclohexanecarboxylic acid 2-(3-diisopropylamino-1-phenylpropyl)-4-hydroxymethylphenyl ester,
(±)-benzoic acid 2-(3-diisopropylamino-1-phenylpropyl)-4-hydroxymethylphenyl ester,
R-(+)-benzoic acid 2-(3-diisopropylamino-1-phenylpropyl)-4-hydroxymethylphenyl ester, (±)-4-methylbenzoic acid 2-(3-diisopropylamino-1-phenyl-propyl)-4-hydroxymethylphenyl ester,
(±)-2-methylbenzoic acid 2-(3-diisopropylamino-1-phenyl-propyl)-4-hydroxymethylphenyl ester,
(±)-2-acetoxybenzoic acid 2-(3-diisopropylamino-1-phenyl-propyl)-4-hydroxymethylphenyl ester,
(±)-1-naphthoic acid 2-(3-diisopropylamino-1-phenylpropyl)-4-hydroxymethylphenyl ester,
(±)-2-naphthoic acid 2-(3-diisopropylamino-1-phenylpropyl)-4-hydroxymethylphenyl ester,
(±)-4-chlorobenzoic acid 2-(3-diisopropylamino-1-phenyl-propyl)-4-hydroxymethylphenyl ester,
(±)-4-methoxybenzoic acid 2-(3-diisopropylamino-1-phenylpropyl)-4-hydroxymethylphenyl ester,
(±)-2-methoxybenzoic acid 2-(3-diisopropylamino-1-phenylpropyl)-4-hydroxymethylphenyl ester,
(±)-4-nitrobenzoic acid 2-(3-diisopropylamino-1-phenylpropyl)-4-hydroxymethylphenyl ester,
(±)-2-nitrobenzoic acid 2-(3-diisopropylamino-1-phenylpropyl)-4-hydroxymethylphenyl ester.

A particular preferred embodiment of the compound of formula (I) is fesoterodine (Ia) or its salts, especially its hydrogen fumarate or its hydrochloride hydrate. In this preferred embodiment, R in formula (I) represents an isopropyl group.

In particular, the present disclosure is concerned with an improvement of the formation of the ester moiety in the synthesis of the compounds of formula (I), wherein a compound of formula (II)

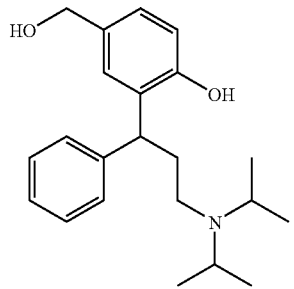

(II)

is reacted with a compound of formula (III)

(III)

wherein R is as defined above, and X is a leaving group. X may be a halogen atom, or a group —O—C(═O)R', or —OR' wherein R' may be selected from hydroxyl, alkyl, aryl, and heteroaryl, and R' is preferably selected from hydroxyl, linear or branched C1-C6 alkyl or phenyl, and wherein R' is most preferably identical to the group R. X is preferably a halogen atom selected from chlorine, bromine and iodine, more preferably chlorine.

In accordance with the present invention, this acylation step is conducted in the presence of N,N-diisopropylethylamine. In a particularly preferred embodiment of the present invention, isobutyric acid chloride is used for the acylation of the compound of formula (II) in the presence of N,N-diisopropylethylamine to give Fesoterodine.

In principle, three different products may be formed by the reaction of the active metabolite which is represented by formula (II) with a compound of formula (III). This is shown in the reaction scheme below:

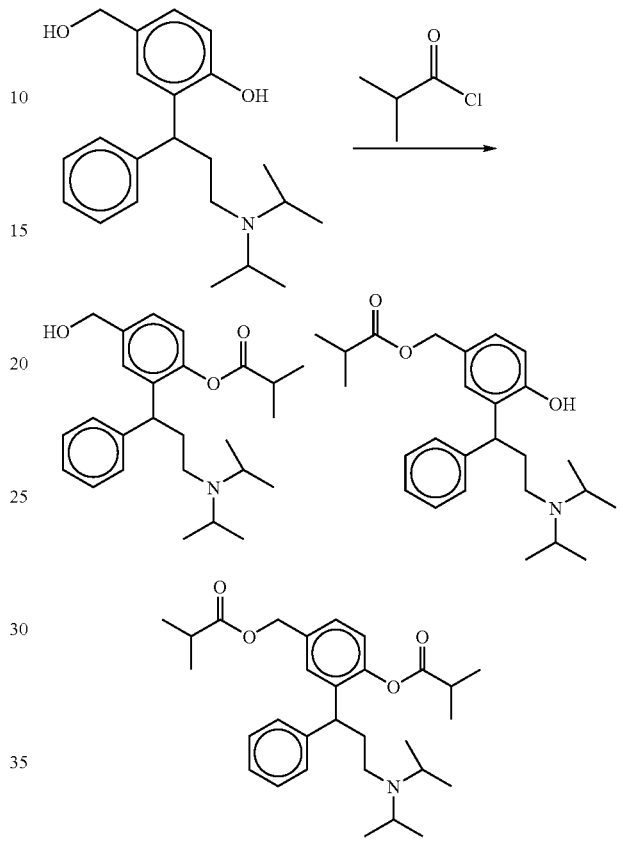

By conducting the acylation reaction in the presence of Huenig's base, the amounts of active metabolite and diester in the reaction product are significantly reduced. In turn, fesoterodine may be obtained in a higher yield and purity, thereby making its production more economic.

The reaction may be conducted under conditions which are similar to the prior art processes and may be suitably chosen by the skilled person.

In a preferred mode of the process according to the disclosure, the reaction is performed at a temperature of −20° C. to 10° C., more preferably −10° C. to 0° C. This increases the content of the compounds of formula (I) in the reaction product.

The reaction (a) is conveniently carried out in a solvent which is preferably selected from methylene chloride, methyl isobutyl ketone, methyl tertiary butyl ketone and methyl tetrahydrofurane. Among these solvents, methylene chloride is particularly preferred.

In another embodiment of the present disclosure, the molar ratio of the compound of formula (III) to the compound of formula (II) is between about 0.95 and about 1.20, preferably not more than about 1.10, thereby reducing the amount of diester by-product formed during the reaction. More preferably, this ratio is between about 1.00 and about 1.05.

In a further preferred embodiment, the process according to the presently disclosed method further comprises a washing step (b), wherein the reaction mixture obtained from step (a) is washed (i) with an alkaline solution, such as sodium carbonate, sodium borate or sodium phosphate, preferably an aqueous solution thereof.

By the use of an alkaline solution, the phenolic monoester of formula (I) which is obtained in the ester formation step in the form of the hydrochloride salt, will be converted into the free base form, thereby rendering it less water soluble.

At the same time, any impurities contained in the reaction product which are more water soluble than the free base form of the monoester of formula (I), in particular any residual of the active metabolite, can be conveniently removed, for example by separating the organic phase containing the compound of formula (I) from the aqueous phase containing most of the impurities.

This further increases the purity of the final product, thereby rendering it particular suitable for use as a drug. Any pharmaceutically acceptable base can be used in this extraction step. Preferred bases are sodium carbonate, sodium hydrogen carbonate, sodium phosphate and sodium borate.

Subsequently, additional washing steps may be performed, e.g. a washing step (ii) using an acidic solution, such as diluted hydrochloric acid. Finally, a third washing step (iii) using basic solutions may be conducted to give the pure free base of the compound of formula (I).

For the convenience of handling and for the incorporation in a pharmaceutical composition, it is preferred that the compound of formula (I) is obtained in a crystalline form. Highly pure, crystalline and stable salts of the phenolic monoesters of formula (I) are describe e.g. in EP 1 230 209. In a further particular preferred embodiment, the process of the present disclosure further comprises a salt formation step (c), whereby the compounds of formula (I) are obtained in the form of an acid addition salt. In an even more preferred embodiment of the present disclosure, this acid addition salt is formed in a crystalline state.

In a particular preferred embodiment of the presently described method, methyl ethyl ketone is used as the solvent for the compound of formula (I) and crystallization is initiated and/or accelerated by the addition of cyclohexane, if necessary.

The use of methyl ethyl ketone and, optionally, of cyclohexane for crystallization allows for the removal of the corresponding diester by-product during the crystallization step. By the use of this particular preferred crystallization procedure, the compounds of formula (I) may be conveniently obtained in a purity that is particularly suitable for use in medicaments.

The process according to the present invention as well as its preferred embodiments will be further illustrated by the following example.

EXAMPLES 1-4

"%" is to be Interpreted as "% (W/W)" Unless Otherwise Indicated 20.0 g of active metabolite is solved in 140 ml dichloromethane (DCM). The temperature of this solution is adjusted to −10° C. Subsequently, a solution of 7.90 g N,N-diisopropylethylamine (Huenig's base) in 40 ml DCM is added, while the temperature rises to −8° C. The reaction solution is again cooled to −10° C., and 6.50 g of isobutyric acid chloride in 120 ml of DCM are added dropwise to the reaction mixture within 30 min, while the temperature is maintained between −8° C. and −10° C. After stirring for 2 h at a temperature of −10° C. to −5° C., the reaction mixture was sampled and analysed by HPLC.

Subsequently, the organic phase is successively washed twice with 100 ml water, 100 ml of a solution of $Na_2CO_3$ (5 wt.-%), and 100 ml of water. After these washing steps, it is separated, filtered and evaporated under reduced pressure using a rotation evaporator and a bath temperature of 50° C. until the weight of the residue remains constant, thereby obtaining 24.83 g of product (yield: 103%). A sample of the reaction product is analysed using HPLC.

HPLC Analysis:

The sample is taken up in a 1:1 mixture of acetonitrile and 0.01 N HCl (e.g. 5 ml acetonitrile and 5 ml 0.01N HCl) and shaken, so as to adjust the amount of fesoterodine to approximately 250 μg per ml acetonitrile. This solution is subjected to HPLC analysis.

Further, a solution of 250 μg of fesoterodine fumarate and of 0.375 μg of each impurity per ml acetonitrile is employed as a reference.

HPLC Parameters:
Column: Polaris C18-Ether, 3 μm, 250 mm×4.6 mm
Eluent A: Water/methanesulfonic acid 1000:0.5 (v/v)
Eluent B: Acetonitrile/methanesulfonic acid 1000:0.5 (v/v)

Typical gradient profile:

| Time (min) | % A | % B |
|---|---|---|
| 0.0 | 67 | 33 |
| 16.0 | 38 | 62 |
| 18.0 | 0 | 100 |

Column temperature: 35° C.
Flow rate: 1.2 mL/min
Detection wavelength: 220 nm
Injection volume: 20 μL
Run time: 22 min The amount of fesoterodine, active metabolite and diester are calculated from the HPLC chromatogram using the area-% method known to the skilled person.

The following response factors have been determined:

| | |
|---|---|
| active metabolite: | 1.4 |
| diester: | 1.1 |
| benzylic ester: | 1.1 |

Reactions were performed in an analogous manner but substituting triethylamine for Huenig's base (Example 3) or without the addition of a base (Example 4). The results are shown in Table 1 below.

TABLE 1

| Ex. | Base | Fesoterodine [%] | Metabolite [%] | Diester [%] |
|---|---|---|---|---|
| 1 | Huenig's base | 97.33 | 0.00 | 2.08 |
| 2 | Huenig's base | 97.80 | 0.02 | 1.73 |
| 3* | Triethylamine | 93.40 | 0.23 | 5.90 |
| 4** | — | 94.70 | 1.90 | 2.90 |

*comparative example according to U.S. Pat. No. 6,713,464
**reference example according to copending application It is clearly derivable from Table 1 above that the present process results in a higher yield and purity of fesoterodine as compared to the process of the prior art.

If the free base of experiment 2 was used to form the hydrogen fumarate using methyl ethyl ketone as the solvent, the crystalline hydrogen fumarate of fesoterodine was obtained in a purity of 99.17%.

The invention claimed is:

1. A process for the preparation of a compound of formula (I) or a salt thereof

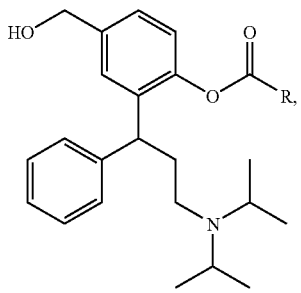
(I)

wherein R is hydrogen, an optionally substituted straight, branched or cyclic $C_1$-$C_6$ alkyl group or an optionally substituted aryl group, comprising
(a) reacting a compound of formula (II)

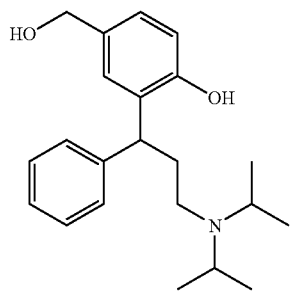
(II)

with a compound of formula (III)

(III)

wherein R is as defined above and X is a leaving group, wherein the reaction is performed in the presence of N,N-diisopropylethylamine.

2. The process of claim 1, wherein X is a halogen atom selected from the group consisting of chlorine, bromine and iodine.

3. The process of claim 1, wherein the reaction is performed at a temperature of −20° C. to 10° C.

4. The process of claim 3, wherein the reaction is performed at a temperature of −10° C. to −0° C.

5. The process of claim 1, wherein the reaction step (a) is carried out in methylene chloride.

6. The process of claim 1, wherein the molar ratio of the compound of formula (III) to the compound of formula (II) is not more than 1.10.

7. The process of claim 1, wherein the molar ratio of the compound of formula (III) to the compound of formula (II) is between 1.00 and 1.05.

8. The process of claim 1, further comprising one or more washing step(s) (b), wherein the reaction mixture obtained from step (a) is contacted with an alkaline solution.

9. The process of claim 8, wherein the washing steps (b) comprise successive washing steps using (i) an alkaline solution, (ii) an acidic solution and (iii) another alkaline solution.

10. The process of claim 8, wherein the washing solution(s) is/are aqueous.

11. The process of claim 1, further comprising a salt formation step wherein a salt of the compound of formula (I) is obtained.

12. The process of claim 11, wherein the salt of the compound of formula (I) is obtained in a crystalline form.

13. The process of claim 12, wherein methyl ethyl ketone is used as a solvent for the compound of formula (I) in the salt formation step.

14. The process of claim 13, wherein the crystallization of the compound of formula (I) in methyl ethyl ketone is initiated by the addition of cyclohexane.

15. The process of claim 1, wherein the compounds of formulae (I) and (II) are the R-enantiomers.

16. The process of claim 1, wherein R is hydrogen, an unsubstituted straight, cyclic or branched $C_1$-$C_6$ alkyl group or wherein R represents a phenyl or naphthyl group, which are unsubstituted or substituted with one or more substituents selected from the group consisting of halogen, $C_1$-$C_6$ alkyl, $C_1$-$C_6$ alkoxyl, nitro and hydroxyl.

17. The process according to claim 1, wherein R is isopropyl.

18. The process of any one of claims 11-14, wherein the salt of the compound of formula (I) is isobutyric acid 2-((R)-3-diisopropylammonium-1-phenylpropyl)-4-(hydroxymethyl) phenylester hydrogen fumarate (fesoterodine hydrogen fumarate).

* * * * *